(12) United States Patent
van Osdol et al.

(10) Patent No.: US 6,699,497 B1
(45) Date of Patent: Mar. 2, 2004

(54) FORMULATIONS FOR THE TRANSDERMAL ADMINISTRATION OF FENOLDOPAM

(75) Inventors: William W. van Osdol, Mountain View, CA (US); Nieves M. Crisologo, Sunnyvale, CA (US); Su Il Yum, Los Altos, CA (US)

(73) Assignee: Alza Corporation, Palo Alto, CA (US)

( * ) Notice: Subject to any disclaimer, the term of this patent is extended or adjusted under 35 U.S.C. 154(b) by 238 days.

(21) Appl. No.: 09/361,026

(22) Filed: Jul. 23, 1999

Related U.S. Application Data

(60) Provisional application No. 60/094,059, filed on Jul. 24, 1998.

(51) Int. Cl.[7] .............................. A61F 13/02; A61K 9/70
(52) U.S. Cl. ........................................ 424/448; 424/449
(58) Field of Search ................................... 424/448, 449

(56) References Cited

U.S. PATENT DOCUMENTS

| | | | |
|---|---|---|---|
| 3,598,122 A | 8/1971 | Zaffaroni | 128/268 |
| 3,598,123 A | 8/1971 | Zaffaroni | 128/268 |
| 3,731,683 A | 5/1973 | Zaffaroni | 128/268 |
| 3,797,494 A | 3/1974 | Zaffaroni | 128/268 |
| 4,031,894 A | 6/1977 | Urquhart et al. | 128/268 |
| 4,197,297 A | 4/1980 | Weinstock | 424/244 |
| 4,201,211 A | 5/1980 | Chandrasekaran et al. | 128/268 |
| 4,286,592 A | 9/1981 | Chandrasekaran | 128/260 |
| 4,314,557 A | 2/1982 | Chandrasekaran | 128/260 |
| 4,379,454 A | 4/1983 | Campbell et al. | 604/897 |
| 4,435,180 A | 3/1984 | Leeper | 604/896 |
| 4,559,222 A | 12/1985 | Enscore et al. | 424/28 |
| 4,573,995 A | 3/1986 | Cheng et al. | 604/896 |
| 4,588,580 A | 5/1986 | Gale et al. | 424/21 |
| 4,645,502 A | 2/1987 | Gale et al. | 604/896 |
| 4,698,062 A | 10/1987 | Gale et al. | 604/896 |
| 4,704,282 A | 11/1987 | Campbell et al. | 424/449 |
| 4,725,272 A | 2/1988 | Gale | 424/448 |
| 4,781,924 A | 11/1988 | Lee et al. | 424/449 |
| 4,788,062 A | 11/1988 | Gale et al. | 424/449 |
| 4,816,258 A | 3/1989 | Nedberge et al. | 424/448 |
| 4,849,226 A | 7/1989 | Gale | 424/448 |
| 4,904,475 A | 2/1990 | Gale et al. | 424/449 |
| 4,908,027 A | 3/1990 | Enscore et al. | 604/890 |
| 4,917,895 A | 4/1990 | Lee et al. | 424/448 |
| 4,938,759 A | 7/1990 | Enscore et al. | 604/896 |
| 4,943,435 A | 7/1990 | Baker et al. | 424/448 |
| 5,004,610 A | 4/1991 | Osborne et al. | 424/448 |
| 5,071,656 A | 12/1991 | Lee et al. | 424/448 |
| 5,122,382 A | 6/1992 | Gale et al. | 424/449 |
| 5,141,750 A | 8/1992 | Lee et al. | 424/448 |
| 5,284,660 A | 2/1994 | Lee et al. | 424/449 |
| 5,314,694 A | 5/1994 | Gale et al. | 424/448 |
| 5,342,623 A | 8/1994 | Enscore et al. | 424/448 |
| 5,635,203 A | 6/1997 | Gale et al. | 424/448 |
| 6,238,693 B1 * | 5/2001 | Luther et al. | 424/448 |

FOREIGN PATENT DOCUMENTS

WO    WO 91/16041    10/1991

* cited by examiner

Primary Examiner—Shelley A. Dodson
(74) Attorney, Agent, or Firm—Vandana Date

(57) ABSTRACT

Composition of matter for application to a body surface or membrane to administer fenoldopam by permeation through the body surface or membrane, the composition comprising fenoldopam to be administered, at a therapeutically effective rate, in combination with a permeation enhancer or mixture. Also disclosed are drug delivery devices and methods for the transdermal administration of fenoldopam for the treatment of hypertension, congestive heart failure, and chronic and acute renal failure.

34 Claims, 6 Drawing Sheets

FORMULATIONS FOR THE TRANSDERMAL ADMINISTRATION OF FENOLDOPAM

RELATED APPLICATIONS

This application claims the benefit of U.S. Provisional Application Ser. No. 60/094,059, filed Jul. 24, 1998.

FIELD OF INVENTION

This invention relates to sustained release formulations for the safe and efficacious administration of fenoldopam for, among other things, the treatment of hypertension, congestive heart failure, and acute and chronic renal failure. More particularly, the invention relates to novel methods, compositions, and devices for transdermally administering fenoldopam to a subject through a body surface or membrane over a sustained time period.

BACKGROUND OF THE INVENTION

The transdermal route of parenteral delivery of drugs and other biologically active agents ("agents") has been proposed for a wide variety of systemically acting and locally acting agents on either a rate-controlled or non-rate-controlled basis and is described in numerous technical publications such as the following: U.S. Pat. Nos. 3,598,122; 3,598,123; 3,731,683; 3,797,494; 4,031,894; 4,201,211; 4,286,592; 4,314,557; 4,379,454; 4,435,180; 4,559,222; 4,573,995; 4,588,580; 4,645,502; 4,698,062; 4,704,282; 4,725,272; 4,781,924; 4,788,062; 4,816,258; 4,849,226; 4,904,475; 4,908,027; 4,917,895; 4,938,759; 4,943,435; 5,004,610; 5,071,656; 5,122,382; 5,141,750; 5,284,660; 5,314,694; 5,342,623; and 5,635,203, the disclosures of which are incorporated in their entirety herein by reference.

When first investigated in depth in the late 1960's, the transdermal route of administration appeared to offer many advantages, particularly with respect to agents that had short half lives and therefore required frequent, repeated dosing or were subject to a high degree of first-pass metabolism by the liver. The peaks and valleys in blood concentration resulting from frequent periodic doses of short half-life agents would be eliminated and replaced by substantially constant plasma concentration. This would not only improve individual compliance but also would eliminate the alternating periods of high side-effects and ineffective blood concentrations associated with periodic dosing. Administering the agent through the skin directly into the blood stream would also eliminate first-pass metabolism of orally administered agents.

It was initially assumed, theoretically, that any short half-life agent of high potency and skin permeability would be suitable for safe and effective transdermal administration. This assumption, however, has not been proven true.

The failure of the transdermal route to fulfill the initial expectations of its potential as an administrative portal was primarily due to the incredible variety of properties with which nature has endowed the skin to permit it to perform its function as the primary barrier to prevent the ingress of foreign substances into the body. See Transdermal Drug Delivery: Problems and Possibilities, B. M. Knepp, et al, CRC Critical Reviews and Therapeutic Drug Carrier Systems, Vol. 4, Issue 1 (1987) and Transdermal Delivery Systems: A Medical Rationale, Gary W. Cleary, Topical Drug Bioavailability, Bioequivalence, and Penetration, Plenum Press, 1993. Thus, the transdermal route of administration, rather than being available to every short half-life agent of high potency and skin permeability, was found to be available only to those few agents that possess the proper combination of a host of characteristics, most of which are unpredictable, required to render the agent suitable for safe and effective transdermal administration.

The most significant of these characteristics are the following:

1. Skin Permeability. The permeability of the skin to the agent must be sufficiently high so that the agent can be administered at a therapeutically effective rate through an area of skin no greater than about 200 $cm^2$ and preferably no greater than 50 $cm^2$. The person-to-person variation in skin permeability at similar sites should also be considered. U.S. Pat. Nos. 4,568,343, 4,746,515, 4,764,379, 4,863,738, 4,865,848, 4,888,354, 4,900,555, 5,378,730, 5,629,019, 5,641,504, 5,686,097, and WO 95/09006, WO 95/01167, WO 96/37231, and WO 96/40259 are related to various compositions and methods for enhancing permeation of drugs through the skin and are hereby incorporated in their entirety by reference.

2. Skin Binding. The skin beneath the transdermal delivery device has the capability of creating a skin depot of drug by absorbing, adsorbing, or binding a certain amount of agent. The amount of agent so bound must be supplied to the skin before the agent can be delivered into the blood stream at steady, therapeutically effective rates. If large amounts of the agent are bound in the skin, significant delays in the onset of therapeutic effect ("lag time") will be observed together with corresponding delays in termination of effect upon removal of the device. The potential also exists for toxic quantities of potent agents to be contained within the skin beneath the device. Skin binding is not related to skin permeability. Agents that are highly permeable may also be highly bound causing a lag time sufficiently long as to render them unsuitable for their intended use.

3. Irritation. The skin reacts to many topically applied substances, particularly those maintained under occlusion, by blistering or reddening accompanied by unpleasant burning, itching, and stinging sensations. Animal models are used to screen for irritation. Animal models, however, often produce both false positives and false negatives. There is also a wide interpersonal variation in susceptibility to irritation. An agent must be minimally irritating in a large percentage of the target population in order to be suitable for safe and effective transdermal administration. U.S. Pat. Nos. 4,552,872, 4,756,710, 5,028,431, 5,130,139, 5,160,741, 5,304,379, and 5,451,407 are directed to overcoming problems of skin irritation associated with transdermal drug delivery and are hereby incorporated in their entirety by reference.

4. Sensitization. Sensitization is an allergic reaction which is induced when an agent is first applied to the skin and is elicited upon continued exposure which may occur immediately or after a long period of seemingly harmless exposure.

The sensitization may be local, elicited by topical exposure, which manifests itself as contact dermatitis accompanied by blistering, itching, reddening and burning at the site of application. More seriously, the sensitization may be systemic, elicited by topical application but manifesting itself by more general allergic reactions at sites other than the site of application. Most seriously, the systemic sensitization may be elicited by oral or intravenous administration of the drug. If the latter occurs, the individual will be unable to take the drug by any route of administration.

Animal models are used to screen for sensitization. Animal models, however, produce both false positives and false negatives. There is also a wide variation in the allergic reaction among individuals as well as between sexes, races and skin types. It is obvious that a useful transdermal agent must be minimally sensitizing in a large percentage of the target population. U.S. Pat. Nos. 5,000,956, 5,049,387, 5,120,145, and 5,149,539 are directed to overcoming sensitization problems associated with transdermal drug delivery by the coadministration of a corticosteroid and are hereby incorporated in their entirety by reference 5. Pharmacokinetic Properties. The half-life of an agent is the time after administration that half of the amount administered has been eliminated from the body. Because blood concentrations of continuously administered agents continue to increase for approximately five half-lives before steady-state constant blood concentrations are achieved, an agent must have a relatively short half-life to be suitable for continuous transdermal administration. The transdermal half-lives of most agents have not been determined. When half-lives of agents determined from intravenous administration are compared with half-lives determined from transdermal administration, the transdermal half-lives are generally longer but there can be wide variation in half-life between individuals based upon factors such as age, sex, health, and body type.

6. Pharmacodynamic Properties. Constant blood levels may not produce the desired therapeutic effects. For example, a therapeutic effect may only be observed at peak blood concentration obtained from bolus dosing but the peak blood or plasma concentration cannot be maintained because of side effects associated therewith. Also, continuous administration of many agents produces tolerance that may require either some agent-free interval or continually increasing and therefore potentially hazardous doses of the agent.

7. Potency. Although a certain degree of potency is required for transdermally administered agent to be effective, it is also possible for an agent to be too potent. As potency increases, lower blood concentrations are required and much smaller quantities are administered. Because of normal inter-individual variations and skin permeability, it may not be possible to precisely control whether a individual is receiving 1 µg/hr or 2 µg/hr, for example. For a highly potent agent, a 1 µg/hr administration may be totally ineffective and a 2 µg/hr rate fatal. Thus, the therapeutic index of an agent, which is the ratio of toxic blood concentration to the therapeutic blood concentration, becomes extremely significant. A highly potent agent should also have a relatively wide therapeutic window in order to be suitable for transdermal administration.

8. Metabolism. One of the perceived advantages of transdermal administration was that it avoided the "first-pass" metabolism of the agent by the liver that is associated with oral administration. It has now been recognized, however, that the skin is also a large metabolizing organ in the body for some drugs. Thus, although first-pass metabolism that occurs after an orally administered agent enters the blood stream can be avoided, skin metabolism, which occurs before the agent enters the bloodstream, cannot be avoided. Skin metabolism is capable of creating metabolites that are inactive, irritating, toxic, or comparable in biological activity to that of the agent. To be suitable for transdermal administration, an agent must have metabolic properties that are consistent with its therapeutic use on continuous administration.

The above summarizes the primary characteristics that effect suitability of an agent for transdermal administration that have been recognized to date. There are undoubtedly others, some of which have not yet been recognized, and, in order for an agent to be suitable for transdermal administration, it must possess the right combination of all these characteristics, a combination of which, as illustrated by the very few drugs that are now suitable for administration from transdermal delivery devices, is quite rare and unpredictable.

The present invention is directed to the transdermal administration of fenoldopam, 6-Chloro-2,3,4,5-tetrahydro-1-(4-hydroxyphenol)-1H-3-benzapine-7,8 diol for the treatment of, among others, hypertension, congestive heart failure, and acute and chronic renal failure. Fenoldopam (Corlopam®) is a renal vasodilator $DA_1$ agonist that produces dose-dependent reduction in systolic and diastolic blood pressure without producing clinically significant increases in heart rate. The elimination half-life of fenoldopam is about 5 minutes in mild to moderate hypertensive patients, with little difference between the R (active) and S isomers. The preparation of fenoldopam is described in U.S. Pat. Nos. 4,197,297, 4,321,195, and 4,705,862, which are hereby incorporated in their entirety by reference.

Currently, fenoldopam is administered by infusion at a maximum rate of up to 1.6 µg/kg min for periods of up to 48 hours. Oral administration does not provide any clinical benefit, thus transdermal administration offers several advantages. For example, transdermal administration of fenoldopam significantly enhances patient compliance by alleviating the discomfort of needles and cumbersome I.V. apparatii by providing a convenient dosage form for once or twice weekly application. Other benefits discussed above associated with the transdermal administration of fenoldopam are also provided, such as sustained blood levels.

DESCRIPTION OF TERMS

As used herein, the term "fenoldopam" intends not only the basic form of fenoldopam but also pharmaceutically acceptable salt forms of fenoldopam, the R or S enantiomers of fenoldopam, either individually or as a racemic mixture, and to mixtures thereof.

As used herein, the term "fenoldopam therapy" intends all medical conditions for which fenoldopam is or will be indicated, including, without limitation, for the treatment of hypertension, congestive heart failure, and acute and chronic renal failure.

As used herein, the term "individual" intends a living mammal and includes, without limitation, humans and other primates, livestock and sports animals such as cattle, pigs and horses, and pets such as cats and dogs.

As used herein, the term "monoglyceride" refers to a monoglyceride or mixture of monoglycerides of $C_{8-20}$ fatty acids and includes, without limitation, glycerol monolaurate (GML), glycerol monooleate (GMO), glycerol monocaprate (GMC), glycerol monocaprylate (GMCL), and glycerol monolinoleate (GMLO).

As used herein, the term "permeation enhancement" intends an increase in the permeability of skin to fenoldopam in the presence of a permeation enhancer as compared to permeability of skin to fenoldopam in the absence of a permeation enhancer.

As used herein, the term "permeation enhancer" intends an agent or a mixture of agents which acts to increase the permeability of the skin to fenoldopam.

As used herein, the term "permeation-enhancing amount" intends an amount of a permeation enhancer which provides permeation enhancement throughout a substantial portion of the administration period.

As used herein, the phrase "predetermined area of skin" intends a defined area of intact unbroken skin or mucosal tissue. That area will usually be in the range of about 5 cm² to about 100 cm².

As used herein the term "salt" intends, but is not limited to, pharmaceutically acceptable organic or inorganic salts. Typical inorganic salts include hydrogen halides such as hydrochlorides, carbonates, phosphates, sulfates, hydrogen sulfates, hydrobromides, nitrates, and sulfides. Organic salts include, but are not limited to, acid addition salts including salts of monocarboxylic and polycarboxylic acids such as acetic acid, malic acid, maleic acid, propionic acid, succinic acid, fumaric acid, citric acid, benzoic acid, cinnamic acid, tartaric acid, and the like.

As used herein, the phrase "sustained time period" or "administration period" intends at least about 8 hours and will typically intend a period in the range of about one to about seven days.

As used herein, the term "therapeutically effective amount" intends the dose of fenoldopam and/or its active metabolites that provides fenoldopam therapy, in the case of adult and juvenile humans, the dosage range is about 1–20 mg fenoldopam per day.

As used herein, the term "therapeutically effective rate" intends a delivery rate of fenoldopam and/or its active metabolites effective to achieve therapeutic blood or plasma levels in an individual during the administration period and is typically within the range of about 0.01–1.6 $\mu$g/kg/min.

As used herein, the term "therapeutic blood or plasma level" intends the level of fenoldopam and/or its active metabolites in blood or plasma that achieves a therapeutic effect for the desired fenoldopam therapy. For individuals with mild to moderate malignant hypertension, this range is about 1–10 ng/mL.

As used herein, the term "transdermal" intends both percutaneous and transmucosal administration, i.e., passage of fenoldopam through a body surface or membrane such as intact unbroken skin or mucosal tissue into the systemic circulation.

SUMMARY OF THE INVENTION

It is an aspect of this invention to provide sustained release formulations to administer a therapeutically effective amount of fenoldopam and/or its active metabolites, over an administration period.

More specifically, it is an aspect of this invention to provide compositions and methods for the transdermal delivery of fenoldopam and/or its active metabolites, and delivery systems for effecting the same, which are suitable for the transdermal administration of fenoldopam and/or its active metabolites continuously through a body surface or membrane at a therapeutically effective rate in order to achieve and maintain therapeutic blood or plasma levels in an individual.

Another aspect of this invention is to improve the compliance of patients in need of fenoldopam therapy by providing compositions, devices, and methods for the transdermal administration of fenoldopam at a therapeutically effective rate.

According to this invention, it has been discovered that fenoldopam can be safely and efficaciously administered transdermally at a therapeutically effective rate to provide, among other things, treatment for hypertension, congestive heart failure, and acute renal failure when coadministered with a suitable permeation enhancer. Therefore, the invention comprises the following aspects, either alone or in combination:

A composition of matter for the transdermal administration of fenoldopam comprising an amount of fenoldopam and a permeation enhancer in a carrier effective to permit sustained release of fenoldopam at a therapeutically effective rate during an administration period in order to administer a therapeutically effective amount of fenoldopam to achieve and maintain therapeutic blood or plasma levels throughout a substantial portion of the administration period.

A device for the transdermal administration of fenoldopam at a therapeutically effective rate, comprising:

(a) a reservoir comprising fenoldopam and a permeation-enhancing amount of a permeation enhancer;

(b) a backing behind the body contacting-distal surface of the reservoir; and (c) means for maintaining the reservoir in fenoldopam transmitting relation with a body surface or membrane, wherein a therapeutically effective amount of fenoldopam is delivered at a therapeutically effective rate during an administration period in order to achieve and maintain therapeutic blood or plasma levels throughout a substantial portion of the administration period.

The permeation enhancer may be any permeation enhancer known in the art to increase permeability of drugs through skin and includes, but is not limited to, those disclosed in the above cited patents. Preferably, the permeation enhancer comprises a permeation enhancing amount of a permeation enhancer including, but not limited to monoglycerides, $C_{10}$–$C_{20}$ fatty acid esters including ethyl palmitate and isopropyl myristate; acyl lactylates such as caproyl lactylic acid and lauroyl lactylic acid; dimethyl lauramide; dodecyl (lauryl) acetate; lactate esters such as lauryl lactate, and myristyl lactate; monoalkyl ethers of polyethyleneglycol and their alkyl or aryl carboxylic acid esters and carboxymethyl ethers such as polyethylene glycol-4 lauryl ether (Laureth-4) and polyethylene glycol-2 lauryl ether (Laureth-2); Myreth-3, myristyl sarcosine, and methyl laurate.

Additionally, the invention is directed to a method for treating an individual suffering from hypertension, congestive heart failure, and/or acute or chronic renal failure comprising transdermally administering fenoldopam to the individual wherein a therapeutically effective amount of fenoldopam is delivered at a therapeutically effective rate during an administration period in order to achieve and maintain therapeutic blood or plasma levels of fenoldopam throughout a substantial portion of the administration period.

These and other aspects of the present invention will be readily apparent from the description and accompanying figures that follow.

DETAILED DESCRIPTION OF THE INVENTION

According to this invention, it has been discovered that fenoldopam can be safely and efficaciously administered by a sustained release formulation. More specifically, it has been found that fenoldopam can be safely and efficaciously administered transdermally at a therapeutically effective rate to provide, among other things, treatment for hypertension, congestive heart failure, and acute renal failure when coadministered with a suitable permeation enhancer. The present invention provides novel compositions, devices, and methods for fenoldopam therapy with improved patient compliance to an individual in need of such therapy.

Therapeutic blood or plasma levels can be obtained from administration rates in the range of 20–1500 µg/hr, preferably about 60–1000 µg/hr. Representative in vitro skin fluxes of fenoldopam through human skin are in the range of about 5 ng/cm$^2$·hr–5.5 µg/cm$^2$·hr, depending on the drug form, permeation enhancer, and adhesive.

This invention finds particular usefulness in administering fenoldopam across skin. It is also useful, however, in administering fenoldopam across mucosa. According to the invention, fenoldopam is placed in fenoldopam transmitting relationship to an appropriate body surface, preferably in a pharmaceutically acceptable carrier thereof, and maintained in place for the desired administration period.

The fenoldopam and permeation enhancer are typically dispersed within a physiologically compatible matrix or carrier, as more fully described below, which may be applied directly to the body as an ointment, gel, cream, suppository or sublingual or buccal tablet. When used in the form of a liquid, ointment, lotion, cream or gel applied directly to the skin, it is preferable, although not required, to occlude the site of administration. Such compositions can also contain other permeation enhancers, stabilizers, dyes, diluents, pigments, vehicles, inert fillers, anti-irritants, excipients, gelling agents, vasoconstrictors, vasodilators, and other components of topical compositions as are known to the art.

In other embodiments, fenoldopam would be administered from a transdermal delivery device as more fully described below. Examples of suitable transdermal delivery devices are illustrated in FIGS. 1–4. In the figures, the same reference numbers are used throughout the different figures to designate the same or similar components. The figures are not drawn to scale.

Figure 1:
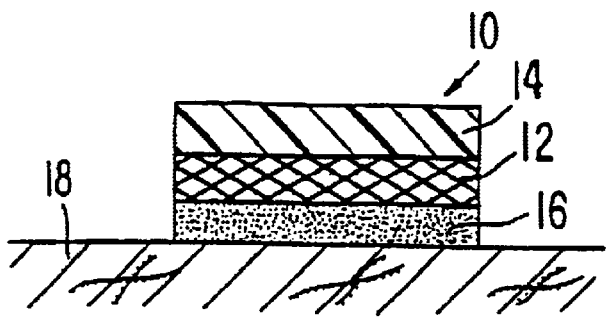
FIG. 1 is a cross-section through a schematic perspective view of one embodiment of a transdermal therapeutic system according to this invention.

Referring now to FIG. 1, a preferred embodiment of a transdermal therapeutic system according to this invention comprises transdermal delivery device 10 comprising a reservoir 12, preferably in the form of a matrix containing fenoldopam, and a permeation enhancer dispersed therein. Reservoir 12 is sandwiched between a backing 14 and an in-line contact adhesive layer 16. The device 10 adheres to the surface of the skin 18 by means of the adhesive layer 16. The adhesive layer 16 may optionally contain the permeation enhancer and/or fenoldopam. A removable release liner (not shown in FIG. 1) is normally provided along the exposed surface of adhesive layer 16 and is removed prior to application of device 10 to the skin 18. Optionally, a rate-controlling membrane (not shown) may be present between the reservoir 12 and the adhesive layer 16. Additionally, a non-rate controlling tie layer membrane as disclosed in U.S. Pat. No. 5,635,203, incorporated herein in its entirety by reference, may be present between the reservoir 12 and adhesive 16 in any of the embodiments depicted in FIGS. 1–4.

Although the preferred embodiments of this invention utilize an in-line adhesive as is shown in FIG. 1, other means for maintaining the system on the skin can be employed. Such means include a peripheral ring of adhesive outside the path of the drug from the system to the skin or the use of other fastening means such as buckles, belts, and elastic arm bands.

Alternatively, reservoir 12 may be in the form of a matrix containing fenoldopam and permeation enhancer dispersed within a suitable adhesive, preferably a pressure sensitive adhesive. Such pressure sensitive adhesives include, but are not limited to, polysiloxanes, polyacrylates, polyurethanes, acrylic adhesives including cross linked or non-crosslinked acrylic copolymers, vinyl acetate adhesives, ethylene vinylacetate copolymers, and natural or synthetic rubbers including polybutadienes, polyisoprenes, and polyisobutylene adhesives, and mixtures and graft copolymers thereof. The matrix formulations according to this embodiment comprise the adhesive containing fenoldopam and permeation enhancer, if present, laminated to a backing on one surface and to a release liner on the other. In addition to the fenoldopam and permeation enhancer, the matrix or carrier may also contain dyes, pigments, inert fillers, anti-irritants, excipients and other conventional components of pharmaceutical products or transdermal devices known to the art. For example, the matrix may also be provided with hydrophilic water absorbing and water soluble polymers known in the art such as polyvinyl alcohol and polyvinyl pyrrolidone individually or in combination. Other suitable water soluble and water absorbing polymers are known in the art, such as those disclosed in U.S. Pat. No. 5,176,916, hereby incorporated in its entirety by reference.

Figure 2:
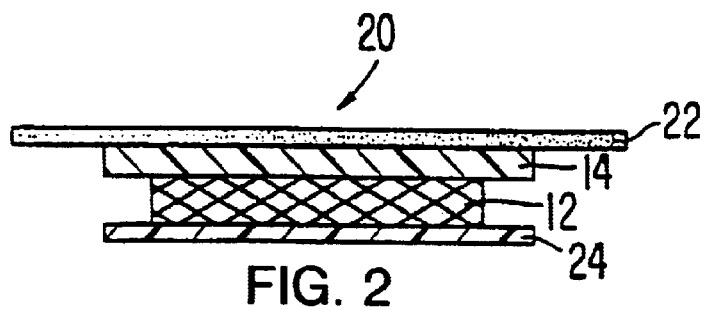
FIG. 2 is a cross-section view through another embodiment of this invention prior to application to the skin.

Alternatively, as shown in FIG. 2, transdermal therapeutic device 20 may be attached to the skin or mucosa of a patient by means of an adhesive overlay 22. Device 20 is comprised of reservoir 12 preferably in the form of a matrix containing fenoldopam and a permeation enhancer dispersed therein. A backing layer 14 is provided adjacent to one surface of reservoir 12. Adhesive overlay 22 maintains the device on the skin and may be fabricated together with, or provided separately from, the remaining elements of the device. With certain formulations, the adhesive overlay 22 may be preferable to the in-line contact adhesive 16 as shown in FIG. 1. Backing layer 14 is preferably slightly larger than reservoir 12, and in this manner prevents the materials in reservoir 12 from adversely interacting with the adhesive in overlay 22. Optionally, a rate-controlling membrane (not shown in FIG. 2) may be provided on the skin-proximal side of reservoir 12. A removable release liner 24 is also provided with device 20 and is removed just prior to application of device 20 to the skin.

Figure 3:
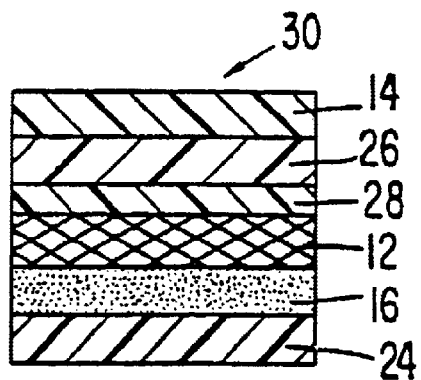
FIG. 3 is a cross-section view through another embodiment of this invention prior to application to the skin.

In FIG. 3, transdermal delivery device 30 comprises a fenoldopam and permeation enhancer reservoir ("fenoldopam reservoir") 12 substantially as described with respect to FIG. 1. Permeation enhancer reservoir ("enhancer reservoir") 26 comprises the permeation enhancer dispersed throughout and contains fenoldopam at or below saturation, when in equilibrium with the fenoldopam reservoir 12.

Enhancer reservoir 26 is preferably made from substantially the same matrix as is used to form fenoldopam reservoir 12. A rate-controlling membrane 28 for controlling the release rate of the permeation enhancer from enhancer reservoir 26 to fenoldopam reservoir 12 is placed between the two reservoirs. A rate-controlling membrane (not shown in FIG. 3) for controlling the release rate of the enhancer and/or fenoldopam from fenoldopam reservoir 12 to the skin may also optionally be utilized and would be present between adhesive layer 16 and reservoir 12.

The rate-controlling membrane may be fabricated from permeable, semipermeable or microporous materials which are known in the art to control the rate of agents into and out of delivery devices and having a permeability to the permeation enhancer lower than that of drug reservoir 12. Suitable materials include, but are not limited to, polyethylene, polyvinyl acetate, ethylene n-butyl acetate and ethylene vinyl acetate copolymers.

Superimposed over the permeation enhancer reservoir 26 of device 30 is a backing 14. On the skin-proximal side of reservoir 12 are an adhesive layer 16 and a removable liner 24 which would be removed prior to application of the device 30 to the skin.

In the embodiments of FIGS. 1, 2 and 3, the carrier or matrix material of the reservoirs has sufficient viscosity to maintain its shape without oozing or flowing. If, however, the matrix or carrier is a low-viscosity flowable material such as a liquid or a gel, the composition can be fully enclosed in a pouch or pocket, as known to the art from U.S. Pat. No. 4,379,454 (noted above), for example, and as illustrated in FIG. 4. Device 40 shown in FIG. 4 comprises a backing member 14 which serves as a protective cover for the device, imparts structural support, and substantially keeps components in device 40 from escaping the device. Device 40 also includes reservoir 12, which contains the fenoldopam and permeation enhancer and bears on its surface distant from backing member 14, a rate-controlling membrane 28 for controlling the release of fenoldopam and/or permeation enhancer from device 40. The outer edges of backing member 14 overlay the edges of reservoir 12 and are joined along the perimeter with the outer edges of the rate-controlling membrane 28 in a fluid-tight arrangement. This sealed reservoir may be effected by pressure, fusion, adhesion, an adhesive applied to the edges, or other methods known in the art. In this manner, reservoir 12 is contained wholly between backing member 14 and rate-controlling membrane 28. On the skin-proximal side of rate-controlling membrane 28 are an adhesive layer 16 and a removable liner 24 which would be removed prior to application of the device 40 to the skin.

Figure 4:
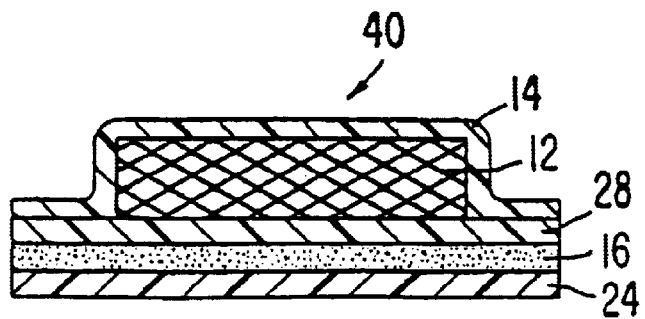
FIG. 4 is a cross-section view through another embodiment of this invention prior to application to the skin.

In an alternative embodiment of device 40 of FIG. 4, reservoir 12 contains the permeation enhancer and contains fenoldopam at or below saturation. The fenoldopam and an additional amount of permeation enhancer are present in adhesive layer 16, which acts as a separate reservoir.

Fenoldopam can be administered to human skin or mucosa by direct application to the skin or mucosa in the form of an ointment, gel, cream or lotion, for example, but are preferably administered from a skin patch or other known transdermal delivery device which contains a saturated or unsaturated formulation of the fenoldopam and enhancer. The formulation may be aqueous or non-aqueous. The formulation should be designed to deliver the fenoldopam and any anti-irritant and/or enhancer at the necessary fluxes. Aqueous formulations typically comprise water or water/ethanol and about 1–5 wt % of a gelling agent, an example being a hydrophilic polymer such as hydroxyethylcellulose or hydroxypropylcellulose. When using aqueous formulations, it is preferable to maintain the pH at less than about 5.5, more preferably between about pH 2–4.5 in order to provide a stable fenoldopam formulation. Typical non-aqueous gels are comprised of silicone fluid or mineral oil. Mineral oil-based gels also typically contain 1–2 wt % of a gelling agent such as colloidal silicon dioxide. The suitability of a particular gel depends upon the compatibility of its constituents with the fenoldopam, anti-irritant, and the permeation enhancer in addition to any other components in the formulation.

The reservoir matrix should be compatible with fenoldopam, the permeation enhancer, and any carrier therefor. The term "matrix" as used herein refers to a well-mixed composite of ingredients. When using an aqueous formulation, the reservoir matrix is preferably a hydrophilic polymer, e.g., a hydrogel.

When using a non-aqueous formulation, the reservoir matrix is preferably composed of a hydrophobic polymer. Suitable polymeric matrices are well known in the transdermal drug delivery art, and examples are listed in the above-named patents previously incorporated herein by reference. A typical laminated system would consist essentially of a polymeric membrane and/or matrix such as ethylene vinyl acetate (EVA) copolymers, such as those described in U.S. Pat. No. 4,144,317, preferably having a vinyl acetate (VA) content in the range of from about 9% up to about 60% and more preferably about 9% to 40% VA. Polyisobutylene/oil polymers containing from 4–25% high molecular weight polyisobutylene and 20–81% low molecular weight polyisobutylene with the balance being an oil such as mineral oil or polybutene may also be used as the matrix material.

The amount of fenoldopam present in the therapeutic device and required to achieve an effective therapeutic result depends on many factors, such as the minimum necessary dosage of the fenoldopam for the particular indication being treated; the solubility and permeability of the matrix, taking into account the presence of permeation enhancer, of the adhesive layer and of the rate-controlling membrane, if present; and the period of time for which the device will be fixed to the skin. The minimum amount of fenoldopam is determined by the requirement that sufficient quantities of fenoldopam must be present in the device to maintain the desired rate of release over the given period of application. The maximum amount for safety purposes is determined by the requirement that the quantity of fenoldopam present must not support a rate of release that reaches toxic levels.

The fenoldopam may be present in the matrix or carrier at a concentration at or below saturation. An excess amount of fenoldopam above saturation may be included in the matrix or carrier, the amount of excess being a function of the desired length of the delivery period of the system. Fenoldopam may be present at a level below saturation without departing from this invention as long as it is continuously administered to the skin or mucosal site at a therapeutic rate and for a period of time sufficient to deliver a therapeutically effective amount of fenoldopam that provides the desired therapeutic result.

The permeation enhancer useful in the present invention is selected from those compounds which are compatible with fenoldopam and which provide enhanced skin permeation to the drug when it is administered together with the drug to the skin of a user. Additionally, the permeation enhancer must not adversely interact with the adhesive of the in-line contact adhesive layer if one is present. Examples of permeation enhancers are disclosed in the patents cited above previously incorporated by reference and can be selected from, but are not limited to, fatty acids, monoglycerides of fatty acids such as glycerol monolaurate, glycerol monooleate, glycerol monocaprate, glycerol monocaprylate, or glycerol monolinoleate; lactate esters of fatty acids such as lauryl lactate, cetyl lactate, and myristyl lactate; acyl lactylates such as caproyl lactylic acid; esters of fatty acids having from about 10 to about 20 carbon atoms, including, but not limited to, isopropyl myristate, and ethyl palmitate; alkyl laurates such as methyl laurate; dimethyl lauramide; lauryl acetate; monoalkyl ethers of polyethyleneglycol and their alkyl or aryl carboxylic acid esters and carboxymethyl ethers such as polyethylene glycol-4 lauryl ether (Laureth-4) and polyethylene glycol-2 lauryl ether (Laureth-2); polyethylene glycol monolaurate; myristyl sarcosine; Myreth-3; and lower $C_{1-4}$ alcohols such as isopropanol and ethanol, alone or in combinations of one or more.

A preferred permeation enhancer according to this invention comprises a monoglyceride of a fatty acid together with a suitable cosolvent, including, but not limited to, lauryl acetate as disclosed in WO 96/40259 and esters of $C_{10}$–$C_{20}$ fatty acids such as lauryl lactate, ethyl palmitate, and methyl laurate. Ethyl palmitate has been found to be particularly desirable as it is obtainable at a high degree of purity, thus providing a purer and better defined permeation enhancer and a system which is more readily characterized. According to a particularly preferred embodiment, the permeation enhancer comprises glycerol monolaurate (GML) and ethyl palmitate within the range of 1–25 wt % and 1–20 wt %, respectively, at a ratio of GML/ethyl palmitate within the range of 0.5–5.0, preferably 1.0–3.5. A particularly preferred embodiment comprises 20 wt % GML and 12 wt % ethyl palmitate.

Another embodiment is directed to the use of surfactant sarcosines, preferably myristyl sarcosine, as a permeation enhancer for pharmaceutically acceptable salts of fenoldopam, preferably fenoldopam mesylate. In general, formulations comprising fenoldopam base were found to be more permeable through the skin as compared to formulations comprising pharmaceutically acceptable salts of fenoldopam such as fenoldopam mesylate. However, formulations comprising myristyl sarcosine as a permeation enhancer for fenoldopam mesylate were found to exhibit higher transdermal fluxes than formulations of the base. Additionally, fenoldopam mesylate when administered transdermally did not exhibit the long lag period observed with fenoldopam base. Thus, according to this embodiment, transdermal compositions, devices, and methods are provided comprising a pharmaceutically acceptable salt of fenoldopam, preferably fenoldopam mesylate, together with a permeation enhancer for the fenoldopam salt, preferably myristyl sarcosine, in order to transdermally administer fenoldopam at therapeutically effective rates and lowered lag time. The use of other surfactant sarcosines such as lauroyl sarcosine, sodium lauryl sarcosine, cocoyl sarcosine, and oleoyl sarcosine are contemplated for use with the compositions, devices, and methods according to this embodiment.

The permeation-enhancing mixture is dispersed through the matrix or carrier, preferably at a concentration sufficient to provide permeation-enhancing amounts of enhancer in the reservoir throughout the anticipated administration period. Where there is an additional, separate permeation enhancer matrix layer as well, as in FIGS. 3 and 4, the permeation enhancer normally is present in the separate reservoir in excess of saturation.

According to another preferred embodiment, an anti-irritant is dispersed throughout the matrix or carrier, preferably at a concentration sufficient to deliver anti-irritant to the skin in an amount effective to reduce skin irritation throughout the anticipated administration period. The anti-irritant is preferably present in excess of saturation in order to ensure that the anti-irritant is continuously administered with the fenoldopam and continues to be present as long as any fenoldopam is present in the epidermis. Suitable anti-irritants include, but are not limited to, methyl nicotinate as disclosed in U.S. Pat. No. 5,451,407, corticosteroids, and buffering agents including ascorbic acid and acetic acid. Such anti-irritants are known in the art as seen in the above cited patents previously incorporated by reference.

For example, if a corticosteroid is used as the anti-irritant, it is preferably administered at a flux within the range of 0.1–5.0 $\mu g/cm^2 \cdot hr$. Hydrocortisone is a preferred corticosteroid and is present in an amount of about 1–5 wt %. The total amount of hydrocortisone administered is not to exceed 5 mg/24 hour in order to avoid possible systemic effects. Hydrocortisone esters such as hydrocortisone acetate are also suitable. More potent corticosteroids may not require a permeation enhancer as hydrocortisone and hydrocortisone acetate do. However, the advantages of hydrocortisone or its esters such as hydrocortisone acetate is that they are approved for over-the-counter use. This invention contemplates the use of any corticosteroid in addition to hydrocortisone and includes, without limitation, beclomethasone, betamethasone, benzoid, betamethasone dipropionate, betamethasone valerate, clobetasol propionate, clobetasol butyrate, desonide, dexamethasone, fluocinonide, prednisolone, and triamcinolone, for example.

Because of the wide variation in skin permeability from individual to individual and from site to site on the same body, it may be preferable that the fenoldopam, anti-irritant, and/or permeation enhancer, be administered from a rate-controlled transdermal delivery device. Rate control can be obtained either through a rate-controlling membrane as described in U.S. Pat. No. 3,797,494 listed above, or through an adhesive or both as well as through other means known in the art.

A certain amount of fenoldopam may bind reversibly to the skin, and it is accordingly preferred that the skin-contacting layer of the device include this amount of fenoldopam as a loading dose.

The surface area of the device of this invention can vary from about 1–200 $cm^2$. A typical device, however, will have a surface area within the range of about 5–60 $cm^2$, preferably about 20 $cm^2$.

The devices of this invention can be designed to deliver fenoldopam effectively for an extended time period of from several hours up to 7 days or longer. Seven days is generally the maximum time limit for application of a single device because the adverse effects of occlusion of a skin site increases with time and the normal cycle of sloughing and replacement of the skin cells occurs in about 7 days.

Preferably, a device for the transdermal administration of fenoldopam, at a therapeutically effective rate, comprises:
  (a) a reservoir comprising:
     (i) 1–50% by weight fenoldopam,
     (ii) 1–50% by weight of a permeation enhancer,
     (iii) 30 to 90% by weight of a polymeric carrier;
  (b) a backing behind the skin-distal surface of the reservoir; and
  (c) means for maintaining the reservoir in fenoldopam—transmitting relation with the skin.

More preferably, a device for the transdermal administration of fenoldopam, at a therapeutically effective rate, comprises:
(a) a reservoir comprising:
 (i) 1–50% by weight fenoldopam,
 (ii) 5–40% by weight of a permeation enhancer,
 (iii) 30–90% by weight of a polymeric carrier;
(b) a backing behind the skin-distal surface of the reservoir; and
(c) means for maintaining the reservoir in fenoldopam—transmitting relation with the skin.

Most preferably, a device for the transdermal administration of fenoldopam, at a therapeutically effective rate, comprises:
(a) a reservoir comprising:
 (i) 5–50% by weight fenoldopam,
 (ii) 5–40% by weight of a permeation enhancer comprising a monoglyceride and a fatty acid ester,
 (iii) 30–90% by weight of a polymeric carrier;
(b) a backing behind the skin-distal surface of the reservoir; and
(c) means for maintaining the reservoir in fenoldopam—transmitting relation with the skin.

The backing may be flexible or nonflexible and may be a breathable or occlusive material. Suitable materials include, without limitation, polyethylene, polyurethane, polyester, ethylene vinyl acetate, acrylonitrile, cellophane, cellulose acetate, cellulosics, ethylcellulose, ethylene vinyl alcohol, plasticized vinylacetate-vinylchloride copolymers, polyethylene terephthalate, nylons, rayon, polypropylene, polyvinyl alcohol, polyvinyl chloride, metalized polyester films, polyvinylidene chloride, polycarbonate, polystyrene, and aluminum foil. The backing may be a multi-laminate film.

The means for maintaining the reservoir in drug and permeation enhancer transmitting relation with the skin is preferably a pressure sensitive adhesive including, but not limited to, polyisobutylene adhesives, silicone adhesives, and acrylate adhesives known in the art including copolymers and graft copolymers thereof. A further embodiment of the invention is directed to including in the adhesive a small percentage, e.g., from about 1 to about 5 wt % of fenoldopam to assure an appropriate initial release rate.

The aforementioned patents describe a wide variety of materials which can be used for fabricating various layers or components of the transdermal fenoldopam delivery systems according to this invention. This invention, therefore, contemplates the use of materials other than those specifically disclosed herein including those which may become hereafter known to the artist capable of performing the necessary functions.

The invention is also directed to a method of continuously administering fenoldopam to a patient at a therapeutically effective rate over an administration period in order to administer a therapeutically effective amount and achieve and maintain therapeutic blood or plasma levels in a patient.

A preferred embodiment of the present invention comprises a method of treating acute or chronic renal failure. According to this embodiment, about 1–6 mg of fenoldopam, preferably 1.5–4 mg, most preferably 2–3 mg, are delivered daily by the compositions, devices, and methods disclosed above. To achieve this result, fenoldopam is delivered at a therapeutic rate within a range of about 20–5500 $\mu$g/hr, preferably about 40–1500 $\mu$g/hr, most preferably 60–600 $\mu$g/hr from a reasonably sized transdermal delivery device having a surface area of less than about 60 $cm^2$ for the treatment period, usually about 6 hours to 5 days, preferably 24–72 hours.

The length of time of fenoldopam presence and the total amount of fenoldopam in the plasma can be changed following the teachings of this invention to provide different treatment regimens. Thus, they can be controlled by the amount of time during which exogenous fenoldopam is delivered transdermally to an individual or animal and the rate at which it is administered.

Having thus generally described our invention, the following specific examples describe preferred embodiments thereof but are not intended to limit the invention in any manner.

EXAMPLE 1

About 3 grams of fenoldopam mesylate was weighed in a 250 ml beaker and dissolved in 120 ml warm distilled water (or to a saturated solution). 3M $Na_2CO_3$ solution was added to the fenoldopam solution drop by drop until the solution reached pH 8.5. The whitened $Na_2CO_3$ solution (converted fenoldopam base) was transferred to a Buchner funnel lined with Whatman #1 filter paper, washed several times with distilled water and vacuum dried at about 65 C. The dried fenoldopam base was transferred into a tared vial and weighed.

Transdermal flux of fenoldopam base and mesylate was measured from polymer matrices containing drug alone and from matrices containing chemical permeation enhancers singly or in combination. Drug reservoirs were prepared by mixing fenoldopam base or mesylate, ethylene vinylacetate (EVA) (USI Chemicals, Illinois) having a vinyl acetate content of 40%, and dodecyl acetate (DA) (Inoue Perfumery Mfg. Co. LTD, Tokyo, Japan), glycerol monolaurate (GML) (Danisco Ingredients), polyvinyl pyrrolidone (PVP) (XL-10, ISP Technologies, Inc., Calvert City, Ky.), lauramide diethanolamine (LDEA), Laureth-2, Laureth-4, Myreth-3, myristyl sarcosine, glycerol monocaprate (GMC), and/or caproyl lactylic acid (CLA) (American Ingredient Co., Grand Viejo, Calif.) in the amounts set forth in Table 1. The resulting mix was then calendered to a 5 mil thickness between 2 release liners. The drug reservoir was then heat laminated to a Medpar® backing on one surface and a 3M acrylate adhesive on the other. Circular systems were cut with a stainless steel punch.

TABLE 1

Fenoldopam Base and Mesylate Formulations

| Formulation No. | Composition | Weight Percentages |
| --- | --- | --- |
| 1 (control) | fenoldopam base/EVA | 15/85 |
| 2 | fenoldopam base/EVA/GML/ML/PVP | 15/37/20/12/16 |
| 3 | fenoldopam base/EVA/Laureth-4 | 15/65/20 |
| 4 | fenoldopam base/EVA/DML | 15/65/20 |
| 5 | fenoldopam base/EVA/MS | 15/65/20 |
| 6 | fenoldopam base/EVA/CLA/LDEA | 15/50/20/15 |
| 7 | fenoldopam base/EVA/Myreth-3 | 15/65/20 |
| 8 | fenoldopam base/EVA/Laureth-2 | 15/65/20 |
| 9 | fenoldopam base/EVA/GMC | 15/65/20 |
| 10 | fenoldopam mesylate/EVA | 15/85 |
| 11 | fenoldopam mesylate/EVA/GML/ML/PVP | 15/37/20/12/16 |
| 12 | fenoldopam mesylate/EVA/Laureth-4 | 15/65/20 |
| 13 | fenoldopam mesylate/EVA/DML | 15/65/20 |
| 14 | fenoldopam mesylate/EVA/MS | 15/65/20 |
| 15 | fenoldopam mesylate/EVA/CLA/LDEA | 15/50/20/15 |
| 16 | fenoldopam mesylate/EVA/Myreth-3 | 15/65/20 |
| 17 | fenoldopam mesylate/EVA/Laureth-2 | 15/65/20 |
| 18 | fenoldopam mesylate/EVA/GMC | 15/65/20 |

Release of fenoldopam from transdermal systems into aqueous medium was measured over 24 hours at 350° C.

The release liner of the matrix system was then removed and each system had its exposed edges masked. The systems were then mounted on a Teflon® holder of a release rate rod using nylon mesh and nickel wire. A known volume of receptor solution (30 ml 0.01 M phosphate buffer solution at pH 2.5) was then placed in a test tube and equilibrated at 35° C. The test tube was placed in a water bath and maintained at 35° C. The Teflon rod with attached system was then reciprocated within the test tube by attaching the rod to a motor which caused constant vertical mixing.

Figure 5:
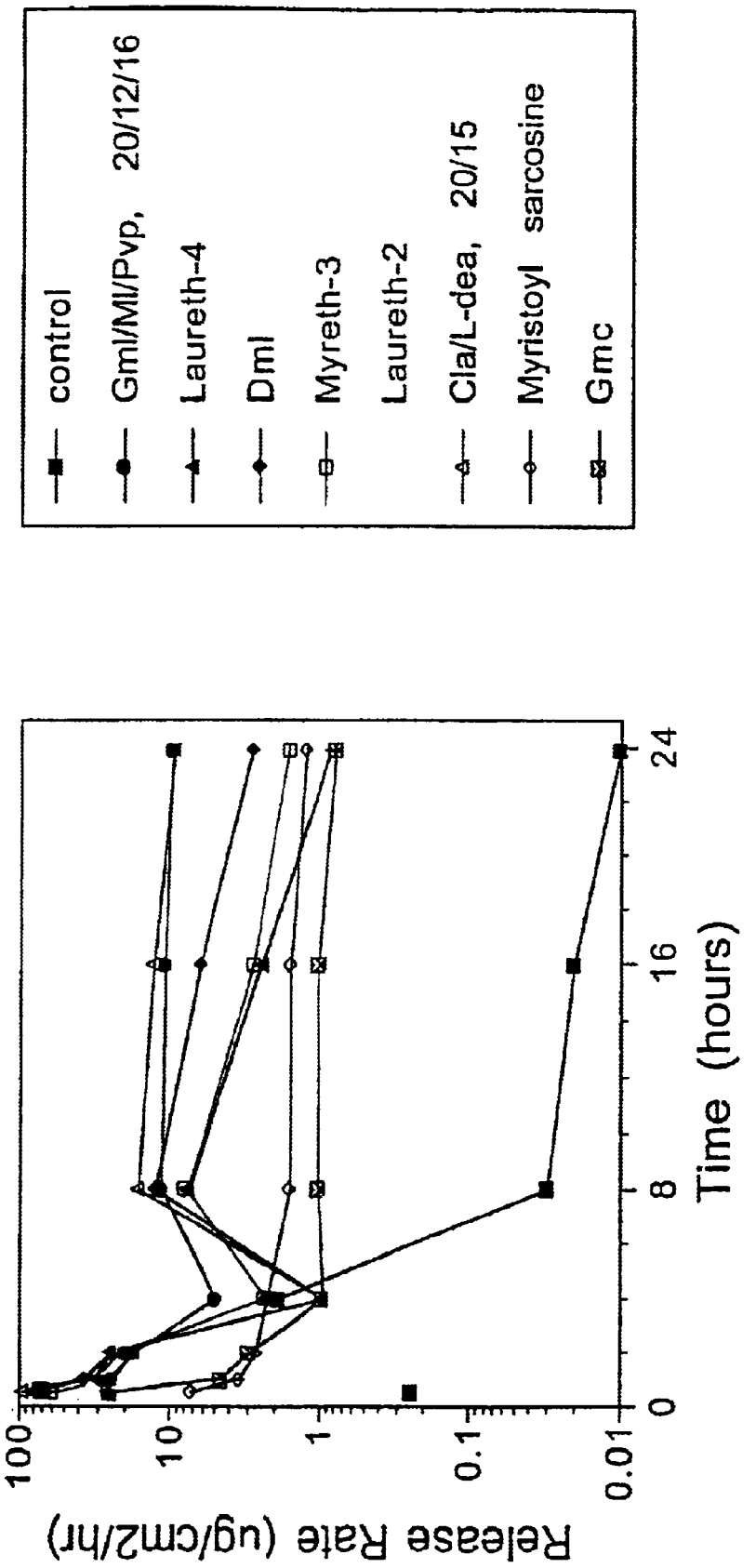
FIG. 5 depicts the release rate of fenoldopam base from polymer matrix formulations containing various permeation enhancers.
Figure 6:
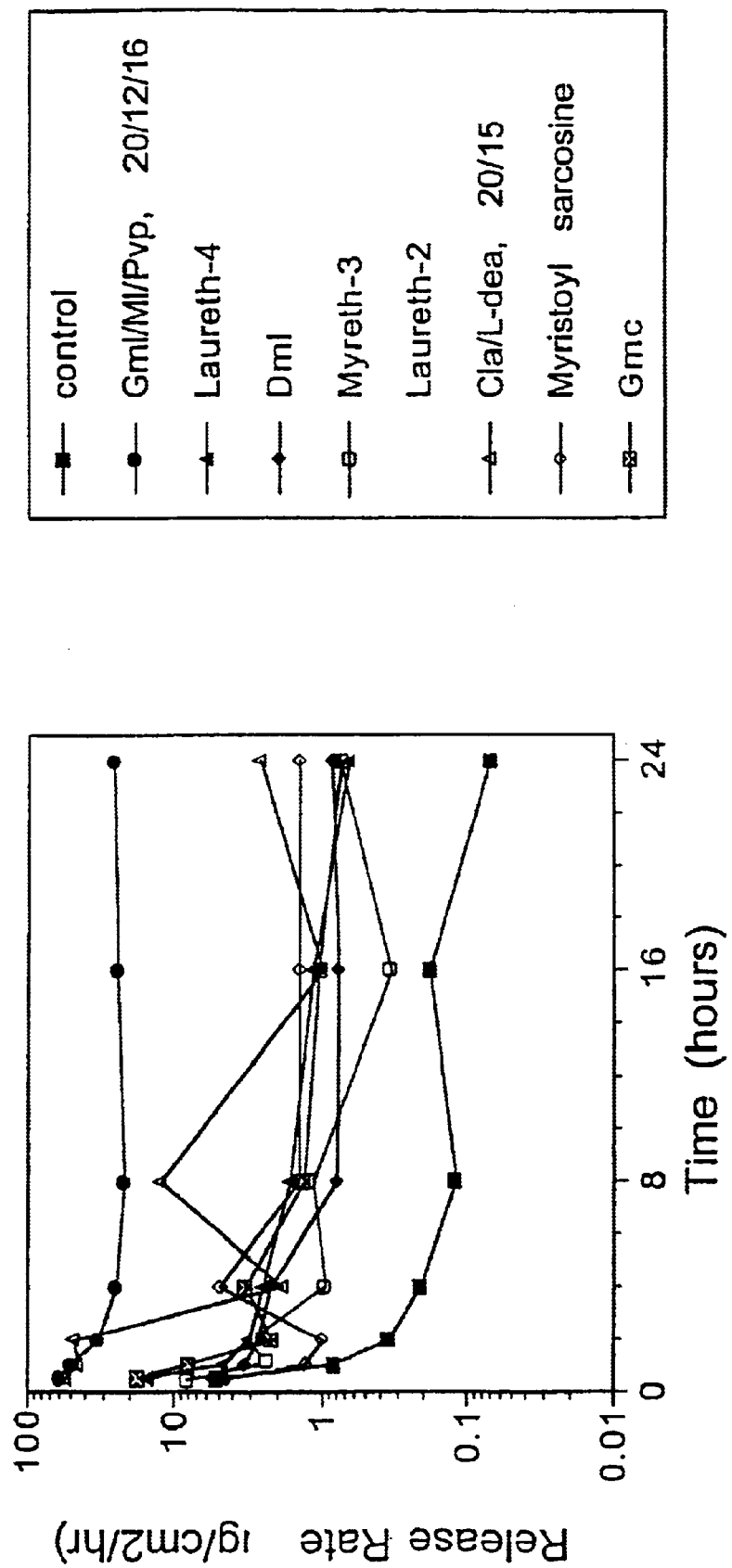
FIG. 6 depicts the release rate of fenoldopam mesylate from polymer matrix formulations containing various permeation enhancers.

At given time intervals, the entire receptor solution was removed from the test tubes and replaced with an equal volume of fresh receptor solutions previously equilibrated at 35° C. The receptor solutions were stored in capped vials at 4° C. until assayed for fenoldopam content by HPLC. From the drug concentration and the volume of the receptor solutions, the area of the system and the time interval, the release rate of the drug from the system was calculated as follows: (drug concentration X volume of receptor)/(area x time) =release rate ($\mu g/cm^2 \cdot hr$). Release rates for the fenoldopam base and mesylate formulations are depicted in FIGS. 5 and 6, respectively.

EXAMPLE 2

Figure 7B:
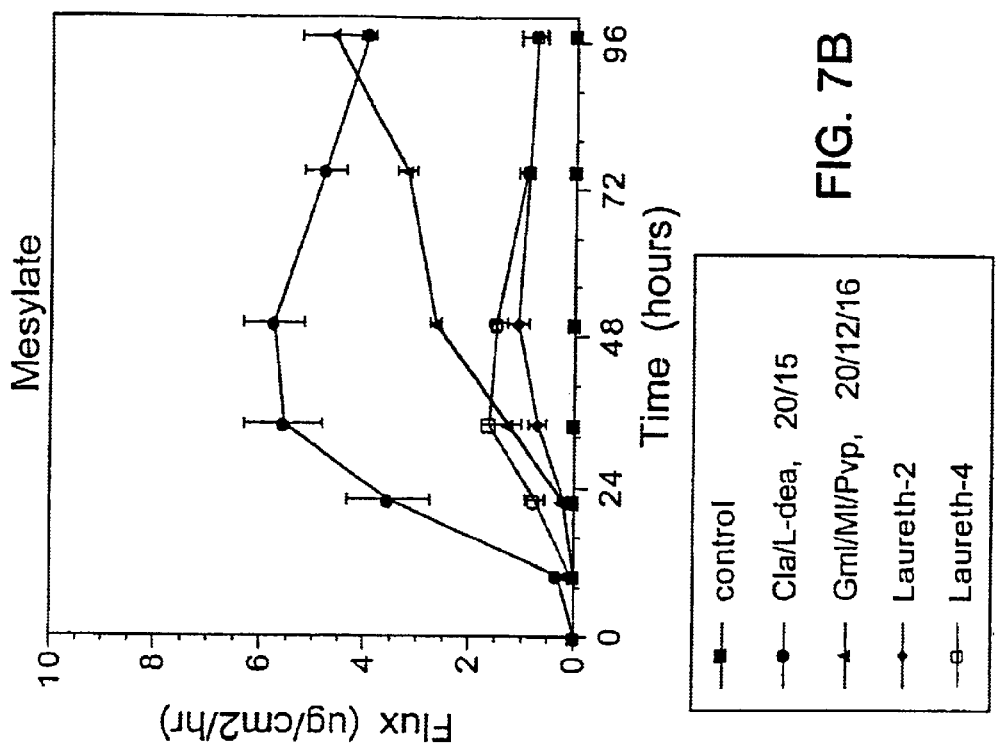
FIGS. 7 and 8 depict the flux of fenoldopam base and mesylate from polymer matrix formulations containing various permeation enhancers.
Figure 7A:
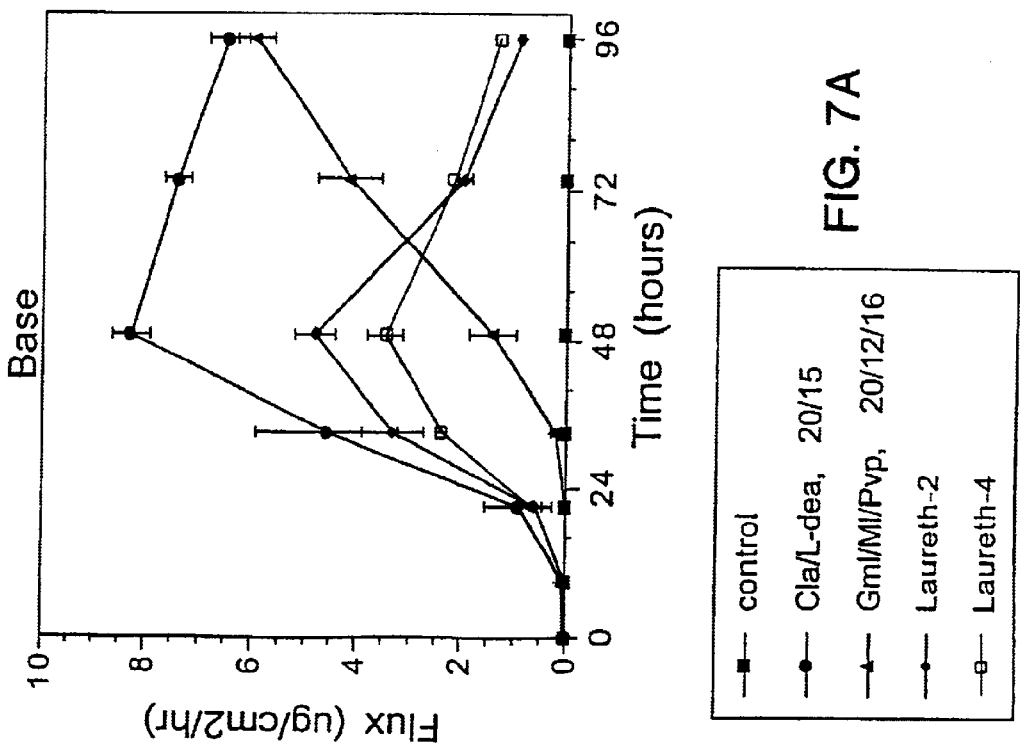
Figure 8B:
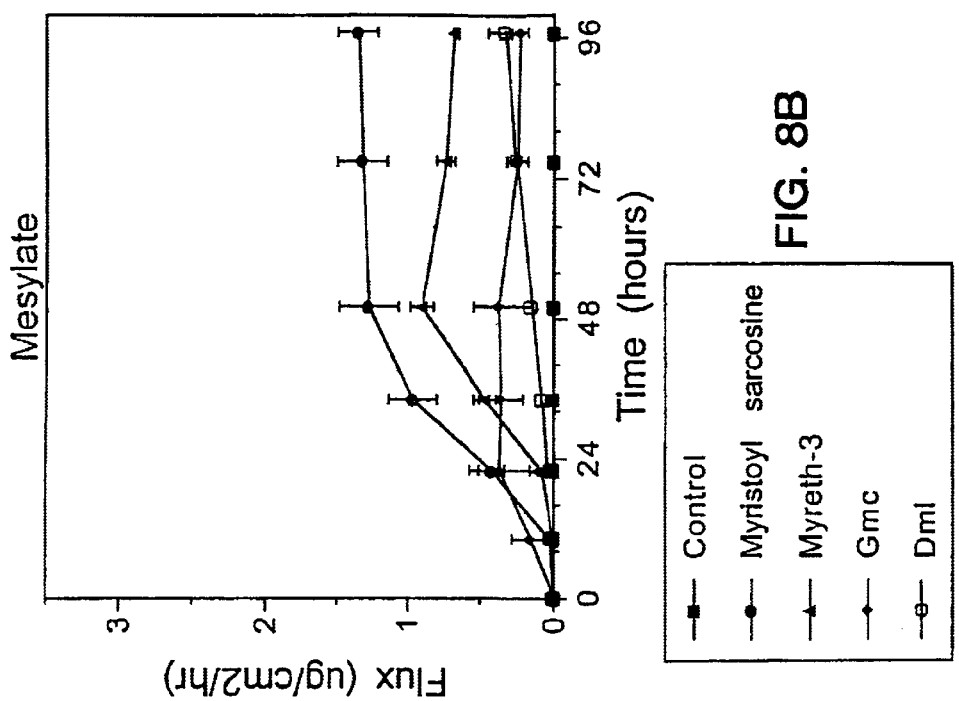
Figure 8A:
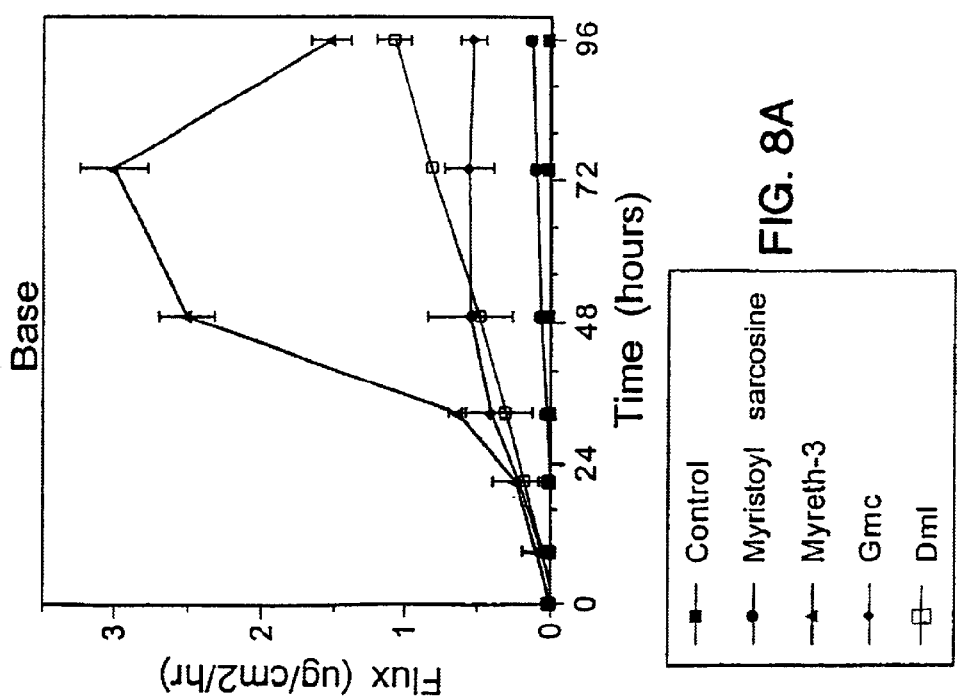

Transdermal systems set forth in Table 1 were prepared according to Example 1 and used to measure permeation through human cadaver skin. Circular pieces of heat stripped human epidermis were blotted dry just prior to use and the stratum corneum surface of the epidermis was applied to the fenoldopam releasing side of the system. The edges of epidermis were then folded around the system so that none of the system edge was exposed to the receptor solution. Fenoldopam permeation through the epidermis was then measured according to the procedure set forth in Example 1. The receptor compartment was filled with a known volume of 0.01 M $KH_2PO_4/K_2HPO_4$ which was adjusted to pH 2.5 with 10% $H_3PO_4$ buffer solution previously equilibrated at 35° C. FIGS. 7 and 8 depict the in vitro transdermal flux of fenoldopam through human epidermis with various permeation enhancers.

EXAMPLE 3

Figure 9:
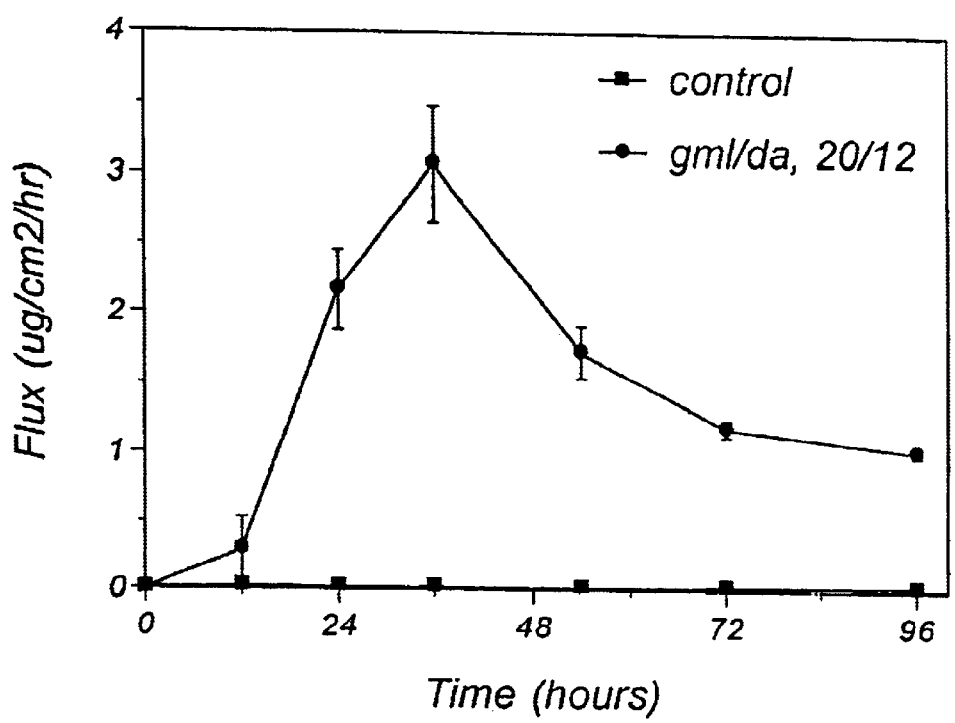
FIG. 9 depicts the flux of fenoldopam base from polymer matrix formulations containing GML and dodecyl acetate (lauryl acetate).

Transdermal systems set forth in Table 2 were prepared according to the procedure set forth in Example 1 and used to measure permeation through human cadaver skin. Circular pieces of heat stripped human epidermis were blotted dry just prior to use and the stratum corneum surface of the epidermis was applied to the fenoldopam releasing side of the system. The edges of epidermis were then folded around the system so that none of the system edge was exposed to the receptor solution. Fenoldopam permeation through the epidermis was then measured according to the procedure set forth in Example 1. The receptor compartment was filled with a known volume of 0.01 M $KH_2PO_4/K_2HPO_4$ which was adjusted to pH 2.5 with 10% $H_3PO_4$ buffer solution previously equilibrated at 35° C. FIG. 9 depicts the mean in vitro transdermal flux of fenoldopam through human epidermis with various permeation enhancers.

TABLE 2

Fenoldopam Base Formulations

| Formulation No. | Composition | Weight Percentages |
|---|---|---|
| 1 (control) | fenoldopam base/EVA | 15/85 |
| 2 | fenoldopam base/EVA/GML/DA | 15/53/20/12 |

Having thus generally described our invention and described certain specific embodiments thereof, including the embodiments that applicants consider the best mode of practicing their invention, it should be readily apparent that various modifications to the invention may be made by workers skilled in the art without departing from the scope of this invention which is limited only by the following claims.

Wherein, what is claimed is:

1. A composition of matter for the transdermal administration of fenoldopam comprising fenoldopam and a permeation enhancing amount of a permeation enhancer in a carrier effective to permit sustained release of fenoldopam at a therapeutically effective rate in order to administer a therapeutically effective amount of fenoldopam in order to achieve and maintain therapeutic blood or plasma levels throughout a substantial portion of the administration period; said composition comprising:
   (a) 5 to 50 weight % of fenoldopam;
   (b) 5 to 40 weight % of a permeation enhancer; and
   (c) 30 to 90 weight % of a polymeric carrier.

2. A composition according to claim 1 comprising a pharmaceutically acceptable salt of fenoldopam.

3. A composition according to claim 2 wherein the salt is fenoldopam mesylate.

4. A composition according to claim 3 wherein the permeation enhancer comprises myristyl sarcosine.

5. A composition according to claim 1 wherein the permeation enhancer comprises a monoglyceride.

6. A composition according to claim 5 further comprising a cosolvent selected from the group consisting of fatty acid esters, caproyl lactylic acid, lauroyl lactylic acid, and dimethyl lauramide.

7. A composition according to claim 6 wherein the monoglyceride is glycerol monolaurate and the cosolvent is selected from the group consisting of dodecyl acetate, lauryl lactate, isopropyl myristate, ethyl palmitate, and methyl laurate.

8. A composition according to claim 1 comprising 5 to 50 weight % fenoldopam base and 5 to 40 weight % of a permeation enhancer comprising a monoglyceride and a fatty acid ester.

9. A compositon according to claim 1 wherein the pH is maintained below 5.5.

10. A composition according to claim 9 wherein the pH is maintained with the range of 2–4.5.

11. A device for the transdermal administration of fenoldopam at a therapeutically effective rate, comprising:
   (a) a reservoir comprising
      (i) 5 to 50 weight % of fenoldopam;
      (ii) 5 to 40 weight % of a permeation enhancer; and
      (iii) 30 to 90 weight % of a polymeric carrier;
   (b) a backing behind the skin contacting-distal surface of the reservoir; and
   (c) means for maintaining the reservoir in fenoldopam transmitting relation with, the skin wherein a therapeutically effective amount of fenoldopam is delivered at a therapeutically effective rate during an administration period in order to achieve and maintain therapeutic blood or plasma levels throughout a substantial portion of the administration period.

12. A device according to claim 11 comprising a pharmaceutically acceptable salt of fenoldopam.

13. A device according to claim 12 wherein the salt comprises fenoldopam mesylate.

14. A composition according to claim 13 wherein the permeation enhancer comprises myristyl sarcosine.

15. A device according to claim 11 wherein the permeation enhancer comprises a monoglyceride.

16. A device according to claim 15 further comprising a cosolvent selected from the group consisting of fatty acid esters, caproyl lactylic acid, lauroyl lactylic acid, and dimethyl lauramide.

17. A device according to claim 16 wherein the monoglyceride is glycerol monolaurate and the cosolvent is selected from the group consisting of dodecyl acetate, lauryl lactate, ethyl palmitate, isopropyl myristate, and methyl laurate.

18. A device according to claim 11 comprising 5 to 50 weight % fenoldopam base and 5 to 40 weight % of a permeation enhancer comprising a monoglyceride and a fatty acid ester.

19. A device according to claim 11 wherein the reservoir comprises a pressure sensitive adhesive which further acts as said means for maintaining the reservoir in fenoldopam transmitting relation with a body surface or membrane.

20. A method for treating an individual in need of fenoldopam therapy comprising transdermally administering a fenoldopam composition to the individual wherein a therapeutically effective amount of fenoldopam is delivered at a therapeutically effective rate during an administration period in order to achieve and maintain therapeutic blood or plasma levels of fenoldopam throughout a substantial portion of the administration period; said composition comprising:

(a) 5 to 50 weight % of fenoldopam;
(b) 5 to 40 weight % of a permeation enhancer; and
(c) 30 to 90 weight % of a polymeric carrier.

21. A method according to claim 20 wherein 1–6 mg/day of fenoldopam are administered.

22. A method according to claim 21 wherein 2–3 mg/day of fenoldopam are administered.

23. A method according to claim 22 for the treatment of acute renal failure.

24. A method according to claim 22 for the treatment of chronic renal failure.

25. A method according to claim 20 wherein fenoldopam is administered at a rate of 20–5500 µg/hr.

26. A method according to claim 25 wherein fenoldopam is administered at a rate of 60–600 µg/hr.

27. A method according to claim 26 wherein the administration period is 24–72 hours.

28. A method according to claim 20 wherein a pharmaceutically acceptable salt of fenoldopam is administered.

29. A method according to claim 28 wherein the salt comprises fenoldopam mesylate.

30. A method according to claim 20 wherein the permeation enhancer comprises a surfactant sarcosine.

31. A method according to claim 30 wherein the permeation enhancer comprises myristyl sarcosine.

32. A method according to claim 20 wherein the permeation enhancer comprises a monoglyceride.

33. A method according to claim 32 further comprising a cosolvent selected from the group consisting of fatty acid esters, caproyl lactylic acid, lauroyl lactylic acid, and dimethyl lauramide.

34. A method according to claim 33 wherein the monoglyceride is glycerol monolaurate and the cosolvent is selected from the group consisting of dodecyl acetate, lauryl lactate, ethyl palmitate, isopropyl myristate, and methyl laurate.

* * * * *